United States Patent
Hartwell et al.

(10) Patent No.: US 11,806,123 B2
(45) Date of Patent: Nov. 7, 2023

(54) SYSTEMS AND METHODS FOR PERFORMING MAGNETIC INDUCTION TOMOGRAPHY

(71) Applicant: Smith & Nephew PLC, Watford (GB)

(72) Inventors: Edward Yerbury Hartwell, Hull (GB); Allan Kenneth Frazer Grugeon Hunt, Beverley (GB)

(73) Assignee: Smith & Nephew PLC, Watford (GB)

( * ) Notice: Subject to any disclaimer, the term of this patent is extended or adjusted under 35 U.S.C. 154(b) by 1018 days.

(21) Appl. No.: 16/614,889

(22) PCT Filed: May 21, 2018

(86) PCT No.: PCT/EP2018/063249
§ 371 (c)(1),
(2) Date: Nov. 19, 2019

(87) PCT Pub. No.: WO2018/215384
PCT Pub. Date: Nov. 29, 2018

(65) Prior Publication Data
US 2020/0155030 A1    May 21, 2020

Related U.S. Application Data

(60) Provisional application No. 62/509,519, filed on May 22, 2017, provisional application No. 62/509,452, filed on May 22, 2017.

(51) Int. Cl.
*A61B 5/0522* (2021.01)
*A61B 5/0536* (2021.01)

(52) U.S. Cl.
CPC .......... *A61B 5/0522* (2013.01); *A61B 5/0536* (2013.01); *A61B 2562/0223* (2013.01)

(58) Field of Classification Search
CPC ................ A61B 5/0522; A61B 5/0536; A61B 2562/0223; G01V 3/104
See application file for complete search history.

(56) References Cited

U.S. PATENT DOCUMENTS 8,384,378 B2  2/2013  Feldkamp et al.
8,452,388 B2  5/2013  Feldkamp et al.
(Continued)

FOREIGN PATENT DOCUMENTS

WO   WO 2017/034708   3/2017
WO   WO 2018/215384   11/2018

OTHER PUBLICATIONS

"Induction Coil Conductivity Sensor Technology Potential for Use in Pressure Ulcer Detection", Advances in MIT Technology—Pressure Ulcer Detection, Fall 2014, pp. 1-6, in 6 pages.
(Continued)

*Primary Examiner* — Peter Luong
(74) *Attorney, Agent, or Firm* — Knobbe, Martens, Olson & Bear, LLP

(57) ABSTRACT

A magnetic inductance tomography (MIT) device for imaging a tissue of a patient can include multiple coils, electronic circuitry, and one or more processors. The electronic circuitry can separately energize individual coils of the multiple coils to generate magnetic fields perturbed by the tissue. The one or more processors can receive MIT signals responsive to the magnetic fields perturbed by the tissue and process the MIT signals to generate an MIT image. The MIT signals can include a first MIT signal generated by a first coil of the multiple coils and a second MIT signal generated by a second coil of the multiple coils. The first MIT signal can be indicative of a characteristic of the tissue at a different depth in the tissue from a surface of the tissue than the second MIT signal.

20 Claims, 13 Drawing Sheets

(56) References Cited

U.S. PATENT DOCUMENTS

| | | | |
|---|---|---|---|
| 8,725,245 B2 | 5/2014 | Feldkamp et al. | |
| 8,773,117 B2 | 7/2014 | Feldkamp et al. | |
| 9,207,197 B2 | 12/2015 | Feldkamp | |
| 9,320,451 B2 | 4/2016 | Feldkamp et al. | |
| 9,442,088 B2 | 9/2016 | Feldkamp et al. | |
| 2008/0258717 A1 | 10/2008 | Igney et al. | |
| 2011/0133731 A1* | 6/2011 | Vauhkonen | G01V 3/104 324/239 |
| 2011/0172512 A1* | 7/2011 | Yan | A61B 5/0522 600/407 |
| 2011/0282609 A1* | 11/2011 | Liu | A61B 5/05 702/65 |
| 2011/0313277 A1* | 12/2011 | Igney | A61B 5/0522 600/410 |
| 2013/0151186 A1 | 6/2013 | Feldkamp | |
| 2015/0241372 A1* | 8/2015 | Feldkamp | A61B 5/0522 702/65 |

OTHER PUBLICATIONS

Feldkamp, J., "Single-coil magnetic induction tomographic three-dimensional imaging", Journal of Medical Imaging, vol. 2(1), Jan.-Mar. 2015, pp. 013502 to 013502-16, in 17 pages.
Invitation to Pay Additional Fees and Partial Search Report, re PCT Application No. PCT/EP2018/063249, dated Aug. 31, 2018.
International Preliminary Report on Patentability for Application No. PCT/EP2018/063249, dated Dec. 5, 2019, 12 pages.
International Search Report and Written Opinion, re PCT Application No. PCT/EP2018/063249, dated Oct. 23, 2018.

\* cited by examiner

SYSTEMS AND METHODS FOR PERFORMING MAGNETIC INDUCTION TOMOGRAPHY

CROSS-REFERENCE TO RELATED APPLICATIONS

This application is a national stage application under 35 U.S.C. § 371 of International Application No. PCT/EP2018/063249, filed on May 21, 2018, and which claims priority to U.S. Provisional Application No. 62/509,452 filed on May 22, 2017, and U.S. Provisional Application No. 62/509,519 filed on May 22, 2017; the disclosures of which are incorporated by reference in their entirety.

BACKGROUND

Embodiments of the present disclosure relate to apparatuses, systems, and methods for the imaging of tissue using magnetic induction tomography (MIT). MIT can involve generating and detecting magnetic fields to measure a distribution of passive electrical properties of an object, such as a tissue of a patient.

BRIEF DESCRIPTION OF THE DRAWINGS

Features and advantages of the present disclosure will be apparent from the following detailed description, taken in conjunction with the accompanying drawings of which.

DESCRIPTION OF EMBODIMENTS

The present disclosure relates to methods and apparatuses for performing magnetic induction tomography (MIT). MIT can involve generating and detecting magnetic fields to map a distribution of passive electrical properties (like conductivity, permittivity, or permeability) of an object, such as a tissue of a patient. MIT can desirably enable one to noninvasively obtain a better understanding of the object. MIT can be performed using one or more dedicated magnetic field generation coils and one or more dedicated magnetic field detection coils, or MIT can be performed using one or more coils that switch between use for generation and detection of magnetic fields. The one or more generation coils can generate a primary magnetic field that passes through an object. The flux of the primary magnetic field can induce eddy currents in the object. The one or more detection coils can then measure a secondary magnetic field generated by the induced eddy currents.

The potential applications of MIT are broad, with various domains of operation including biomedicine, industrial process tomography and non-destructive evaluation. For instance, wound healing is natural process performed by the human body in response to injury. The amount of time taken for a wound to heal can be dependent on many different factors, which include the human body's ability to heal itself and any treatments that are applied to the wound to accelerate wound healing. Understanding the healing status of a wound and being able to monitor the healing process, such as through use of MIT, can help to inform decisions on treatment of the wound and assist in the development of future wound therapies.

Figure 1:
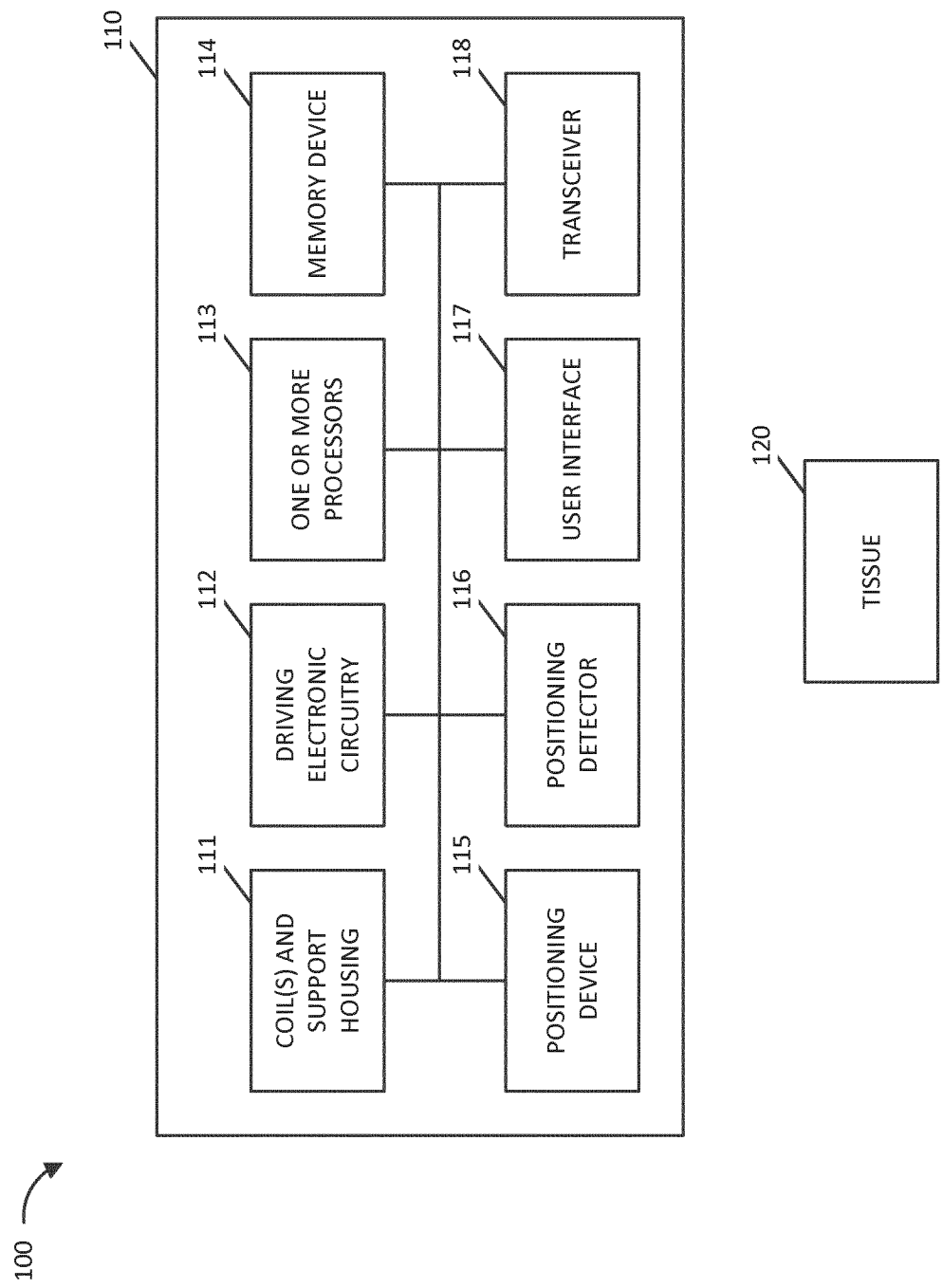
FIG. 1 schematically illustrates a system including a magnetic induction tomography (MIT) device and a tissue of a patient.

FIG. 1 illustrates a system 100 comprising a MIT device 110 and a tissue 120 of a patient. The MIT device 110 can be positioned next to the tissue 120 and be used to noninvasively determine electrical characteristics of the tissue 120 at different depths in the tissue 120 from a surface of the tissue 120. The electrical characteristics can be used by the MIT device 110 to generate a three-dimensional MIT image of the tissue 120. The tissue 120 may, for example, have been damaged by a tumor or because the patient was positioned too long in the same position causing tissue damage near a bone of the patient. The tissue 120 can be positioned in one or more different configurations, such as under compression or not under compression, or different orientations when the MIT device 110 determines electrical characteristics of the tissue 120.

The MIT device 110 can include a coil(s) and support housing 111, driving electronic circuitry 112, one or more processors 113, a memory device 114, a positioning device 115, a positioning detector 116, a user interface 117, and a transceiver 118. In some implementations, the MIT device 110 can include a subset of the components of the MIT device 110 illustrated in FIG. 1 rather than all of the components. The MIT device 110 can be of a size and weight that facilitates hand placement or carrying of the MIT device 110 by the patient with relative ease.

The coil(s) and support housing 111 can include one or more coils and a support housing configured to support the one or more coils. The one or more coils can be configured and positioned for generation or detection of magnetic fields. The one or more coils can be concentric or non-concentric. The support housing can be composed of a material, such as a plastic or cloth, that may minimally or may not interfere with neighboring magnetic fields.

The driving electronic circuitry 112 can energize the one or more coils of the coil(s) and support housing 111 to generate magnetic fields by supplying a voltage and current to the one or more coils. The driving electronic circuitry 112 can individually or separately energize one of the one or more coils, a subset of the one or more coils, or all of the one or more coils. As a result, the driving electronic circuitry 112 can over time control the shape and intensity characteristics of the magnetic fields generated by the one or more coils of the coil(s) and support housing 111. Moreover, each coil, each subset of the one or more coils, or all of the one or more coils when energized can generate a magnetic field that may be perturbed differently by the tissue 120 than when a different coil or subset of coils of the one or more coils may be energized.

In some implementations, one or more of the coils that may not be energized can be shorted. In yet other implementations, one or more of the coils that may not be energized can be supplied with a voltage or current different from a voltage or current supplied to the one or more coils that are energized.

The one or more processors 113 can control the driving electronic circuitry 112 to energize one or more coils of the coil(s) and support housing 111. For example, the one or more processors 13 can selectively or sequentially cause the driving electronic circuitry 112 to energize one of the one or more coils, a subset of the one or more coils, or all of the one or more coils.

The one or more processors 113 can detect variations in the magnetic field around the one or more coils of the coil(s) and support housing 111 by detecting variations in a voltage across one or more coils or a current output from one or more of the coils due to perturbations by the tissue 120. The variations in the voltage or the current can be indicative of the passive electrical properties of the tissue 120. The one or more processors 113 can process the variations to determine electrical properties of the tissue 120, which may be, for instance, indicative of whether the tissue is living or dead. As part of the processing, the one or more processors 113 can utilize analysis methods like Eulerian magnification, such as is described with respect to at least FIGS. 3, 4A, 4B, and 5 in U.S. Provisional Patent Application No. 62/506,551, titled "WOUND ANALYSIS DEVICE AND METHOD", filed May 15, 2017, which is incorporated by reference herein in its entirety.

As different particular coils of the one or more coils of the coil(s) and support housing 111 are energized, each of the different particular coils can generate a different magnetic field that may be more significantly perturbed by electrical properties at a different detection area away from the coil(s) and support housing 111. By matching the perturbation in each different magnetic field with its corresponding different detection area, the one or more processors 113 can detect electrical properties at the corresponding different detection areas and thus assign the electrical properties the corresponding different detection areas. Such an approach can be used by the one or more processors 113 to detect properties of the tissue 120 at different areas of the tissue 120, such as at different depths from a surface of the tissue 120. In one example, a coil having a diameter of 2.5 in. and placed on the surface of a skin of a patient can be used to detect electrical properties beneath the skin at a depth of around 6 cm.

The one or more processors 113 can cause the driving electronic circuitry 112 to selectively or sequentially energize one of the one or more coils, a subset of the one or more coils, or all of the one or more coils. From the detected magnetic field variations as different particular coils of the one or more coils of the coil(s) and support housing 111 are energized, the one or more processors 113 can generate a three-dimensional MIT image of the tissue 120. In some implementations, the MIT image can be around a 3 cm×3 cm×3 cm image of the tissue 120, a 5 cm×5 cm×5 cm image of the tissue 120, or a 10 cm×10 cm×10 cm image of the tissue 120.

The memory device 114 can include volatile or nonvolatile memory used to store instructions or data for the driving electronic circuitry 112 or the one or more processors 113, for example.

The positioning device 115 can be used to control and adjust a position of the coil(s) and support housing 111.

The positioning detector 116 can be used to detect a position or orientation of the MIT device 110, such as a position or orientation of one or more components of the MIT device 110 with respect to one or more other components of MIT device 110. The positioning detector 116 can provide the detected position or orientation to the one or more processors 113 so that the one or more processors 13 can account for the detected position or orientation when controlling the driving electronic circuitry 112 or processing the variations to determine electrical properties of the tissue 120 (for instance, by assigning a confidence or quality indication associated with the variations or determined electrical properties or removing artifacts). In one example, the positioning detector 116 can include one or more transducers used in position detection.

The user interface 117 can include one or more inputs or one or more outputs for a user to control operations of the MIT device 110.

The transceiver 118 can be used to receive input data at the MIT device 110 and provide output data from the MIT device 110. The transceiver 118 can communicate wirelessly or via wired communication. The transceiver 118 can include an input port and an output port which can be the same or different ports.

Figure 2A:
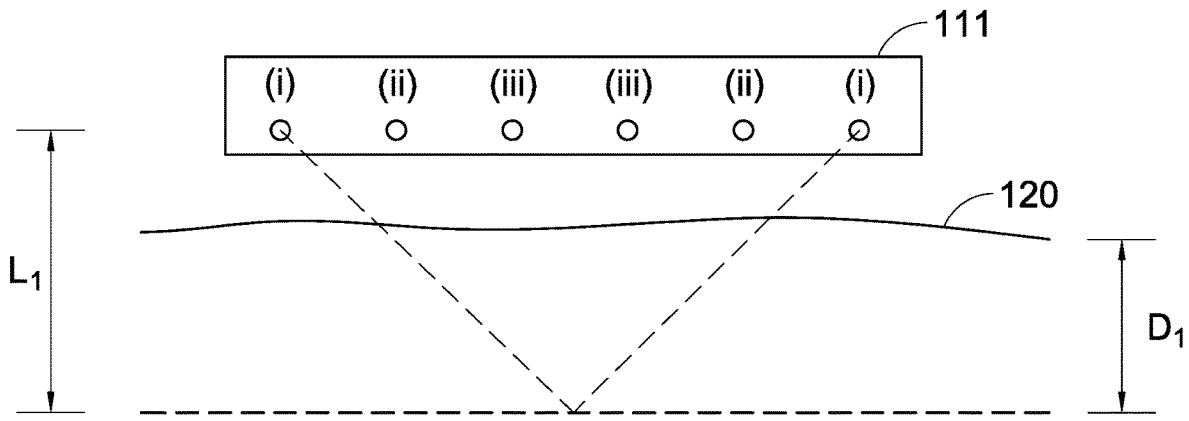
FIGS. 2A, 2B, and 2C illustrate components of a system, such as the system of FIG. 1, that includes concentric coils contained within a coil housing.
Figure 2B:
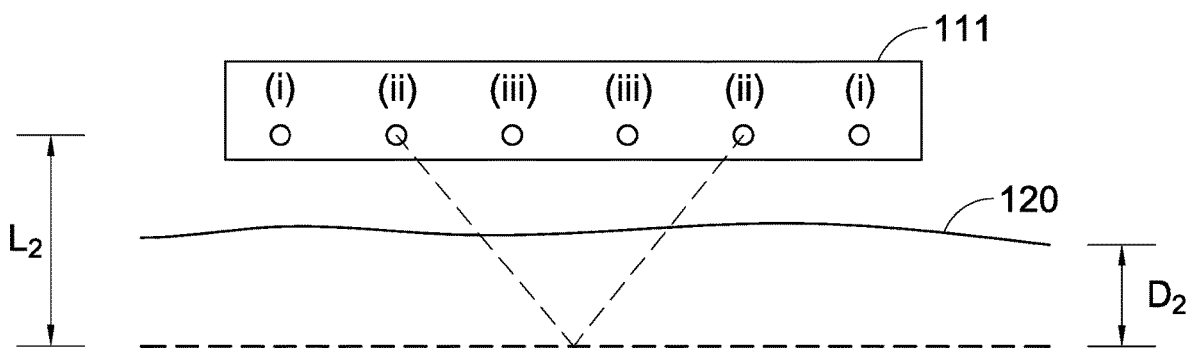
Figure 2C:
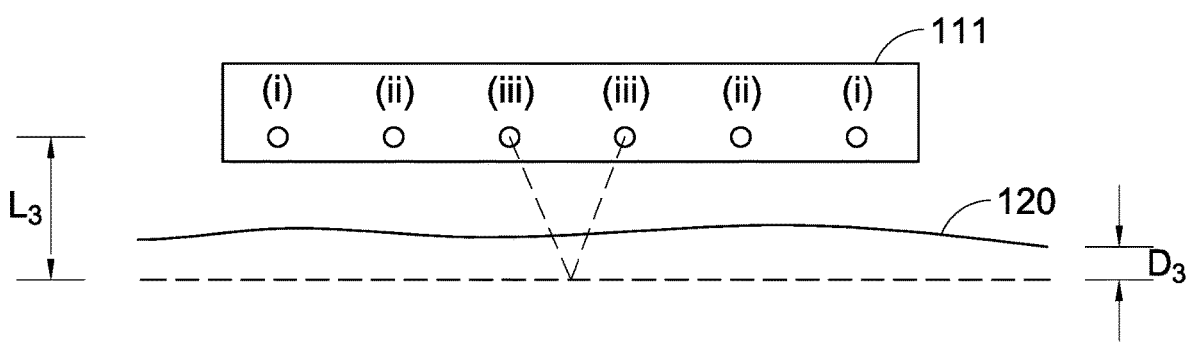

FIGS. 2A-C illustrate cross-sectional views of an embodiment of some components of the system 100 of FIG. 1. The coil(s) and support housing 111 is shown in FIGS. 2A-C as including a first coil (i), a second coil (ii), and a third coil (iii) that are part of or contained within a coil housing. The first coil (i), second coil (ii), and third coil (iii) can be concentric with respect to one another. As described above with respect to FIG. 1, the one or more processors 113 can cause the driving electronic circuitry 112 to energize the first coil (i), second coil (ii), or third coil (iii). The distance between the coil(s) and support housing 111 and the tissue 120 may remain constant in FIGS. 2A-C; however, the individual coils of the coil(s) and support housing 111 can be separately energized from FIG. 2A, to FIG. 2B, to FIG. 2C. FIGS. 2A-C, moreover, demonstrate how increasing the diameter of the magnetic field generation or detection coil can increase the distance at which the coil(s) and support housing 111 can detect electrical properties of the tissue 120.

As can be seen from FIG. 2A, the coil(s) and support housing 111 can be used to detect electrical properties of the tissue 120 at a first length L1 from the coil(s) and support housing 111 and at a first depth $D_1$ from a surface of the tissue 120 when the first coil (i) that has the greatest diameter is energized and the other coils are not energized. As can be seen from FIG. 2B, the coil(s) and support housing 111 can be used to detect electrical properties of the tissue 120 at a second length $L_2$ from the coil(s) and support housing 111 and at a second depth $D_2$ from the surface of the tissue 120 when the second coil (ii) is energized and the other coils are not energized. As can be seen from FIG. 2C, the coil(s) and support housing 111 can be used to detect electrical properties of the tissue 120 at a third length $L_3$ from the coil(s) and support housing 111 and at a third depth $D_3$ from the surface of the tissue 120 when the third coil (iii) that has the smallest diameter is energized and the other coils are not energized. The first depth $D_1$ can be greater than the second depth $D_2$, and the second depth $D_2$ can be greater than the third depth $D_3$. In such a manner, the imaging depth can vary while maintaining a consistent distance between the coil(s) and support housing 111 and the tissue 120.

Figure 3:
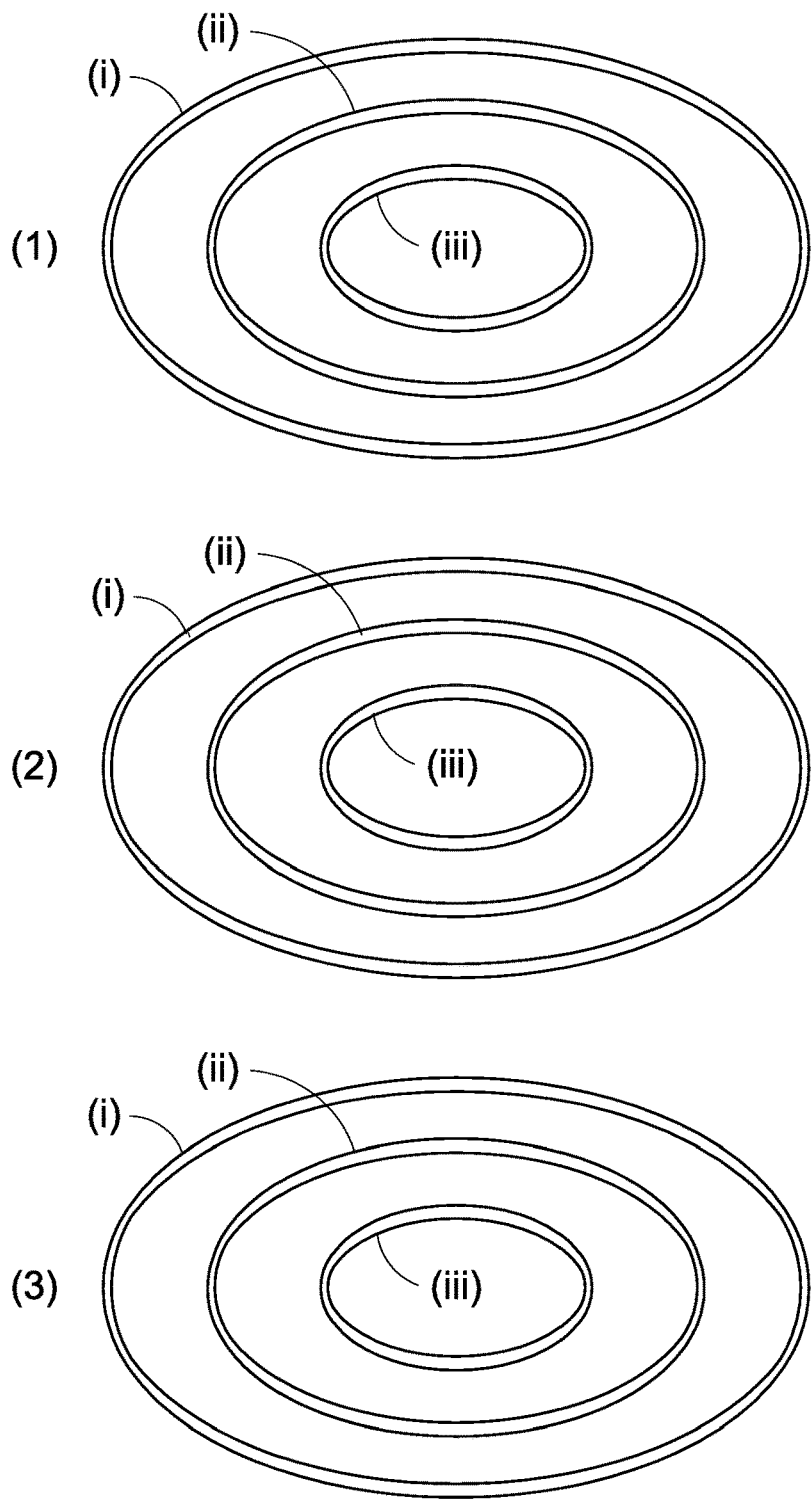
FIG. 3 illustrates an exploded view of concentric coil sets in a stacked configuration.

FIG. 3 illustrates an exploded view of an embodiment including three sets or levels of concentric coils 320, 330, 340 that can be positioned in the coil(s) and support housing 111 of FIG. 1. The coil(s) and support housing 111 can include three first coils (i), three second coils (ii), and three third coils (iii). One of the first coils (i), one of the second coils (ii), and one of the third coils (iii) in FIG. 3 can together form one of three levels of a stack of coils that includes a first level, a second level and a third level. The coils of one level can be energized as described with respect to FIGS. 2A-C to enable the coil(s) and support housing 111 to detect electrical properties of the tissue 120 at different depths in the tissue 120 using the coils of the one level. Moreover, all of the coils of one level can be simultaneously energized to detect electrical properties of the tissue 120 at a first depth, and all of the coils of another level can be simultaneously energized to detect electrical properties of the tissue 120 at a second depth different from the first depth. In other implementations, one or more of the first level 310, second level 320 and third level 330 can be offset relative to one another so that, for example, a center axis of the coils of one level may not align with the center axis of the coils of one or more other levels. Optionally, the coil(s) and support housing 111 can be rotated during operation, as described elsewhere herein, as one or more of the first level 310, second level 320 and third level 330 are energized to detect electrical properties in the tissue 120.

Figure 4:
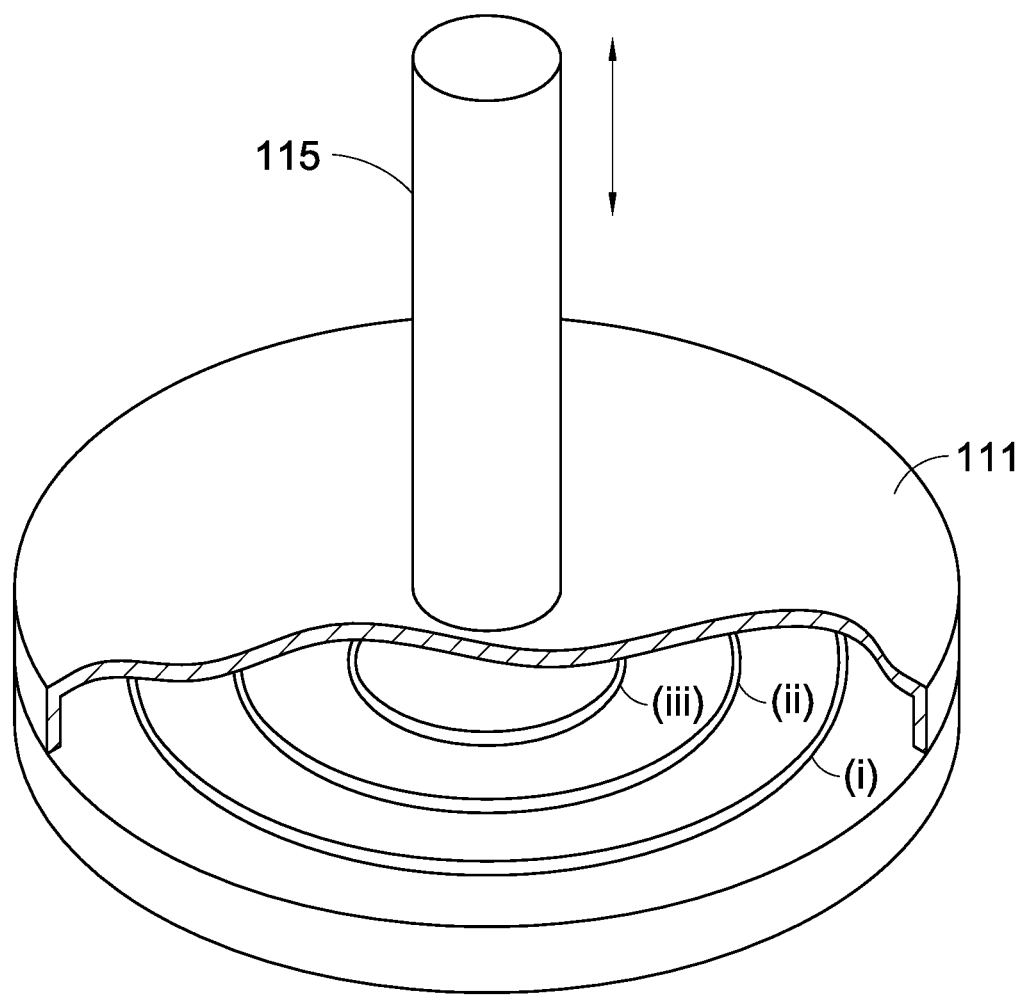
FIG. 4 illustrates a partial cut-away view of support housing, coils, and a positioning device of a system, such as the system of FIG. 1.

FIG. 4 illustrates an embodiment of the coil(s) and support housing 111 and the positioning device 115 of FIG. 1. The positioning device 115 as shown can include an elongate member coupled to the coil(s) and support housing 111. The elongate member can move, such as in a reciprocating manner up and down, to vary a distance between the coil(s) and support housing 111 and the tissue 120. An actuator (not shown) can be used to control the movement of the elongate member. The elongate member can be partly or entirely non-metallic and include a piston or a threaded screw, such as a PTFE (Polytetrafluoroethylene) lead screw. The piston or threaded screw can, for example, be partly or entirely non-metallic. In some instances, the elongate member can move continuously, and the coil(s) and support housing 111 can be used to generate or detect magnetic fields while the elongate member is moving. In yet other instances, the elongate member can move when the coil(s) and support housing 111 is not being used to generate or detect magnetic fields, and thus the elongate member can remain stationary while the coil(s) and support housing 111 is being used to generate or detect magnetic fields (for example, before the elongate member moves the one or more coil(s) to a different location).

Figure 5:
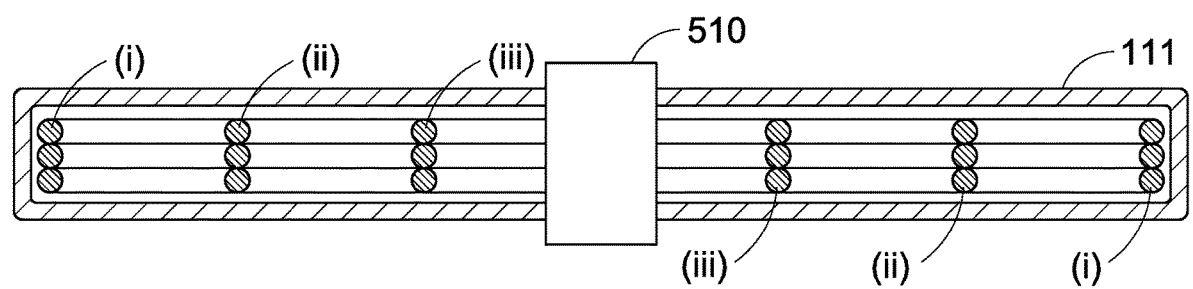
FIG. 5 illustrates a cross-sectional view of a support housing, coils, and a ferromagnetic core of a system, such as the system of FIG. 1.

FIG. 5 illustrates a cross-sectional view of an embodiment of the coil(s) and support housing 111 of FIG. 1. The coil(s) and support housing 111 as shown can include a core 510, such as a ferromagnetic core, extending along an axis of one or more coils of the coil(s) and support housing 111. An actuator (not shown) can axially move the core relative to the one or more coils to alter the magnetic field generated by the coil(s) and support housing 111 and used to detect electrical properties of the tissue 120. In some implementations, the core can (i) extend in a direction other than the direction that the core extends in FIG. 5 (for instance, at an angle or perpendicular relative to the axis of the one or more coils), (ii) be positioned at another location other than the location of the core illustrated in FIG. 5 (for instance, off-center relative to a center of the one or more coils), (iii) have a shape other than the shape of the core illustrated in FIG. 5 (for instance, another geometric shape like a sphere or cube or a non-geometric), (iv) include two, three, four, or more different cores that move separately or independently, or (v) rotate about one or more rotation axis to alter the magnetic field generated by the coil(s) and support housing 111.

Figure 6A:
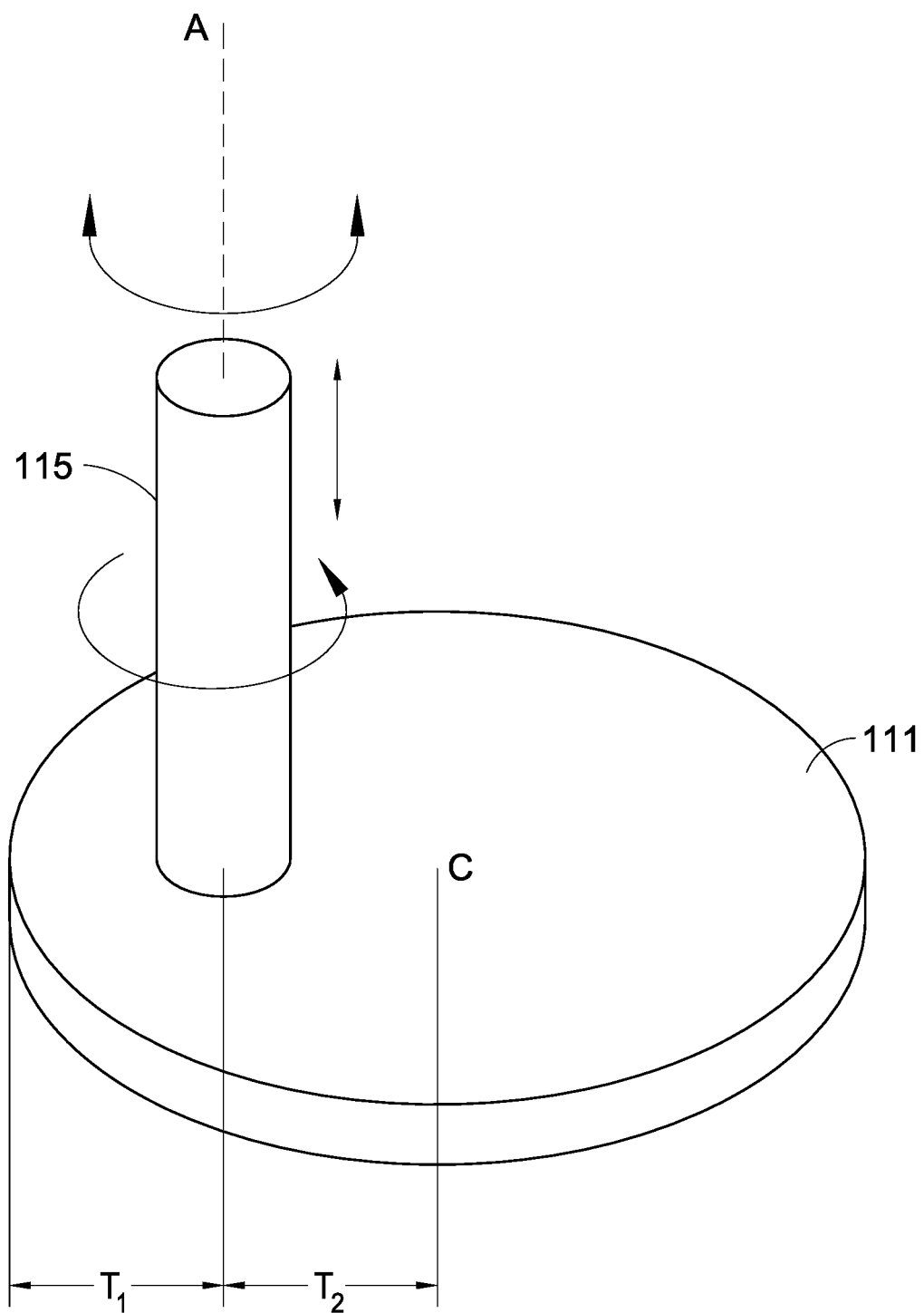
FIGS. 6A, 6B, and 6C illustrate a support housing and positioning device of a system, such as the system of FIG. 1.

FIG. 6A illustrates an embodiment of the coil(s) and support housing 111 and the positioning device 115 of FIG. 1. The positioning device 115 as shown can include a rotatable member that rotates about an axis A. The coil(s) and support housing 111 can be mounted to the rotatable member off-center of the axis A by a distance $T_2$ from a center C of the coil(s) and support housing 111. A distance $T_1$ can extend a diameter of the coil(s) and support housing 111 (or one more coil contained therein) less the distance $T_2$. The distances $T_1$ and $T_2$ can be varied to control the range of motion of the coil(s) and support housing 111 and the area over which the coil(s) and support housing 111 can detect electrical properties of the tissue 120. Advantageously, in certain embodiments, the structure of the coil(s) and support housing 111 and the positioning device 115 shown in FIG. 6A can enable the coil(s) and support housing 111 to generate or detect magnetic fields over a distance that is up to two times the diameter of the one or more coils of the coil(s) and support housing 111 as compared to an implementation where the coil(s) and support housing 111 is stationary.

Figure 6B:
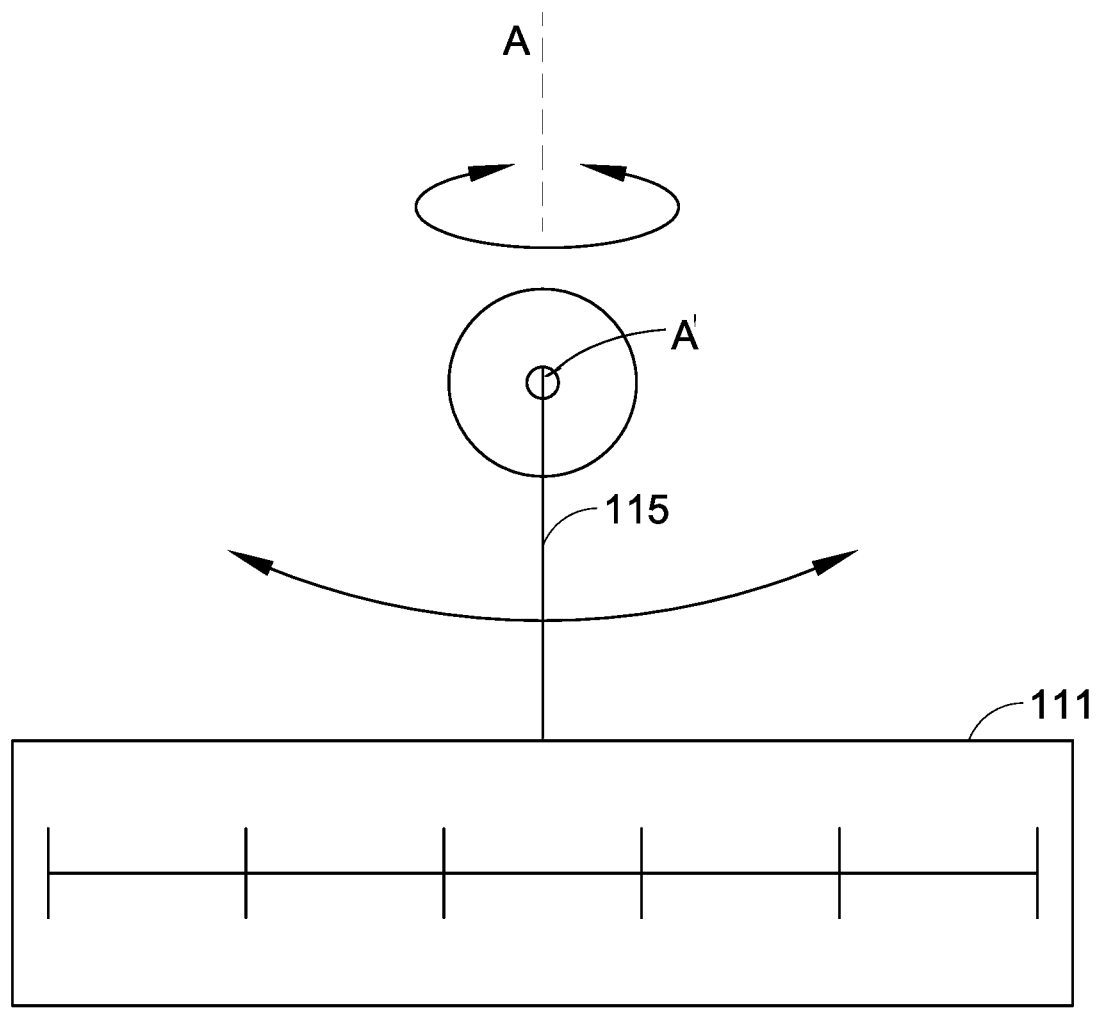

FIG. 6B illustrates an embodiment of the coil(s) and support housing 111 and the positioning device 115 of FIG. 1. The positioning device 115 as shown can include multiple movable members, including one member that rotates about at least an axis A and another member that pivots about a point A'. As a result, the coil(s) and support housing 111 can vary the area over which the coil(s) and support housing 111 detects electrical properties of the tissue 120.

Figure 6C:
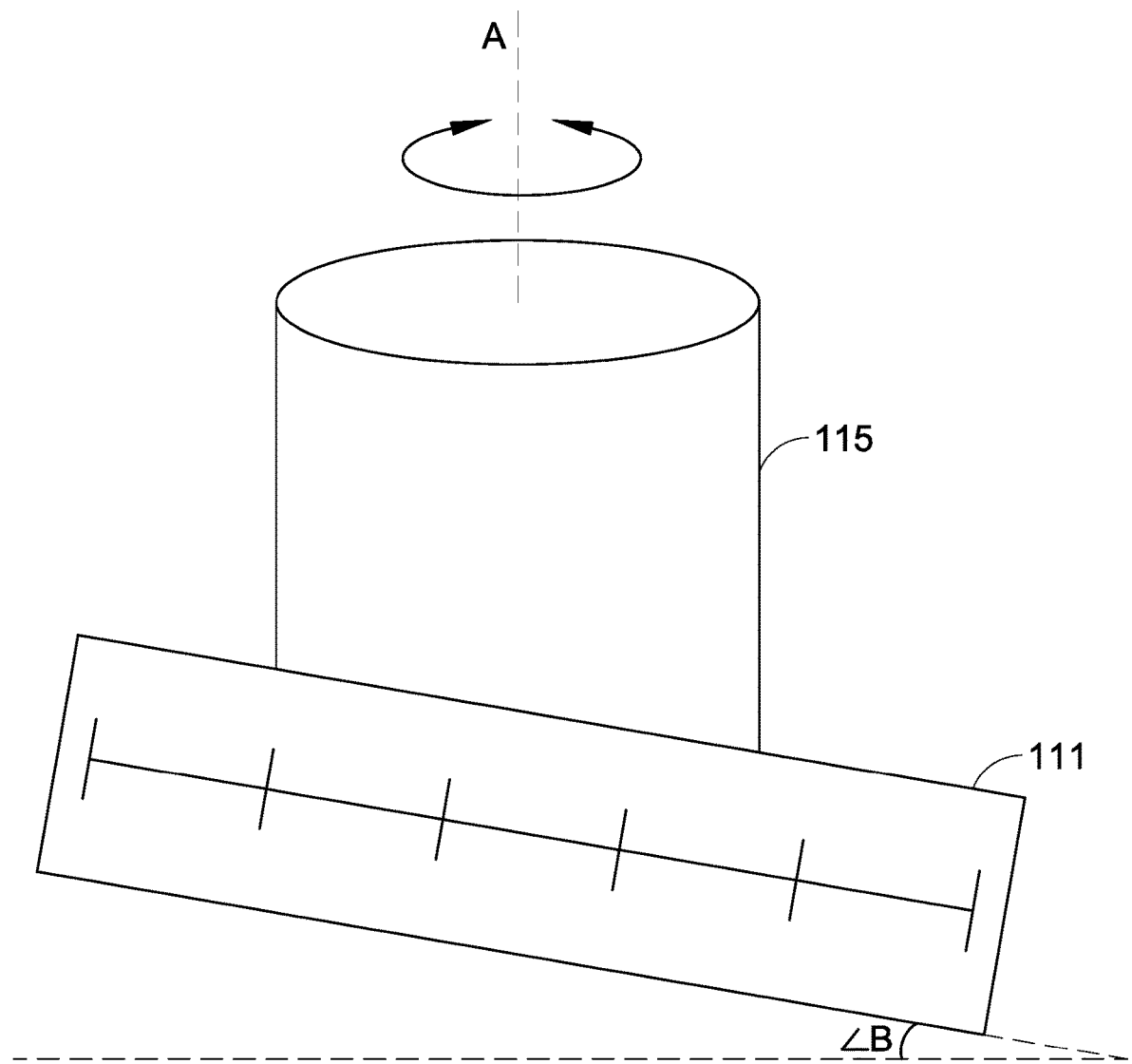

FIG. 6C illustrates an embodiment of the coil(s) and support housing 111 and the positioning device 115 of FIG. 1. The positioning device 115 as shown can include a rotatable member that rotates about an axis A and has an angled bottom face, which can be angled at an angle ∠B relative to a surface like a flat surface or a skin of patient. The angle ∠B can, for example, be an angle within the range of 0° to 90°, such as 10°, 20°, 30°, 40°, 50°, 60°, 70°, or 80°.

Figure 7A:
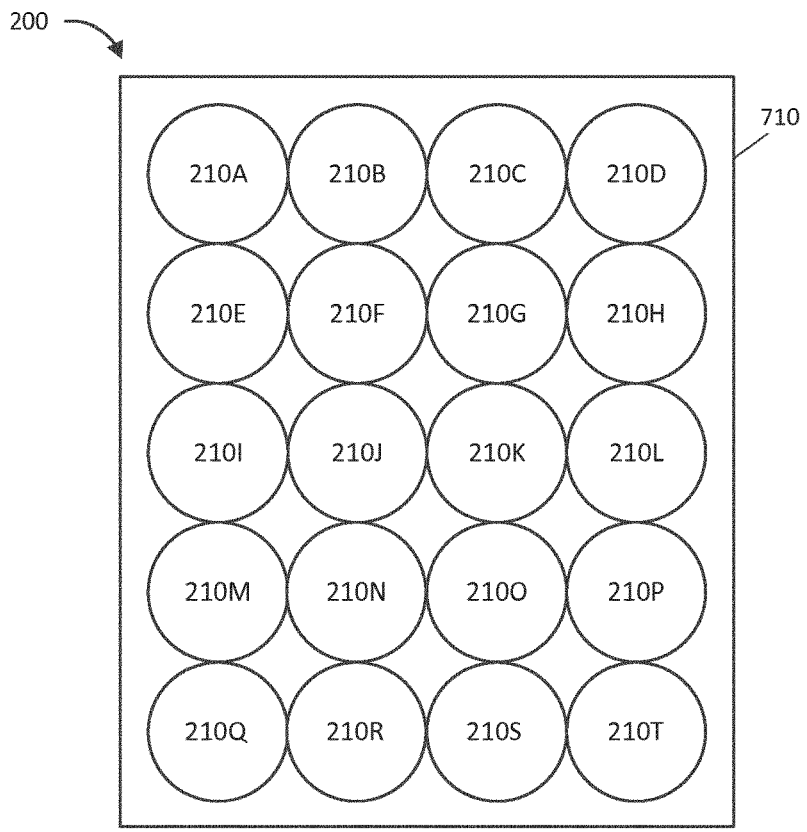
FIGS. 7A and 7B illustrate a MIT device that may be part a system, such as the system of FIG. 1, and attached to skin of a patient and includes coils contained within a coil housing and arranged in an array.
Figure 7B:
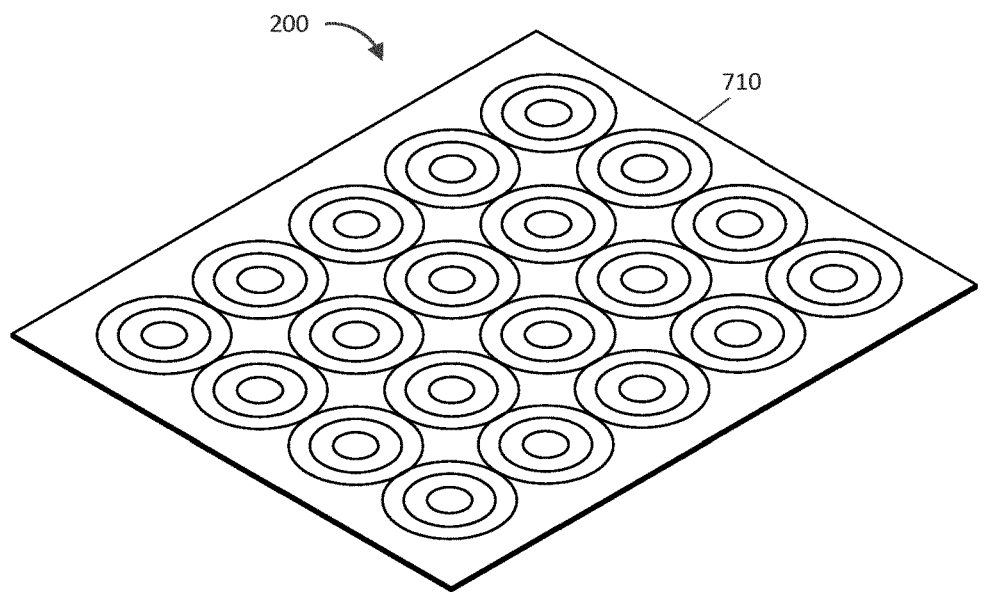

FIGS. 7A and 7B illustrate a device 200 attachable to a skin of a patient for use in MIT of a tissue of the patient. The device 200 can illustrate one example implementation of the coil(s) and support housing 111 of FIG. 1. The device 200 as shown in FIG. 7A includes multiple coils 210A-210T that are part of or contained within a coil housing 710 and arranged in an array. The coil housing 710 can be a material layer that may be flexible and configured to conform to a curvature of the skin. The coils 210A-210T can be integrally formed in the coil housing 710. In some embodiments, the coils 210A-210T are coupled to the coil housing 710 through adhesives or structural design of the coil housing. The coils 210A-210T can vary in size and diameter or can be of all of a similar size and diameter in some implementations.

As illustrated in FIGS. 7A and 7B, the multiple coils 210A-210T can be arranged in parallel rows. FIG. 7A depicts a top view of the device 200, and FIG. 7B depicts a perspective view of the device 200 with coils 210A-210T. In one implementation, the device 200 can be part of a wound dressing or placed above or underneath a wound dressing used to cover and seal a wound prior to applying negative wound pressure therapy to the wound. In another implementation, the device 200 can be part of a drape attachable to skin of a patient and/or securely attached to the skin or an object near the skin using, for example, one or more of an adhesive, a fastener, gravity, or friction.

Figure 8:
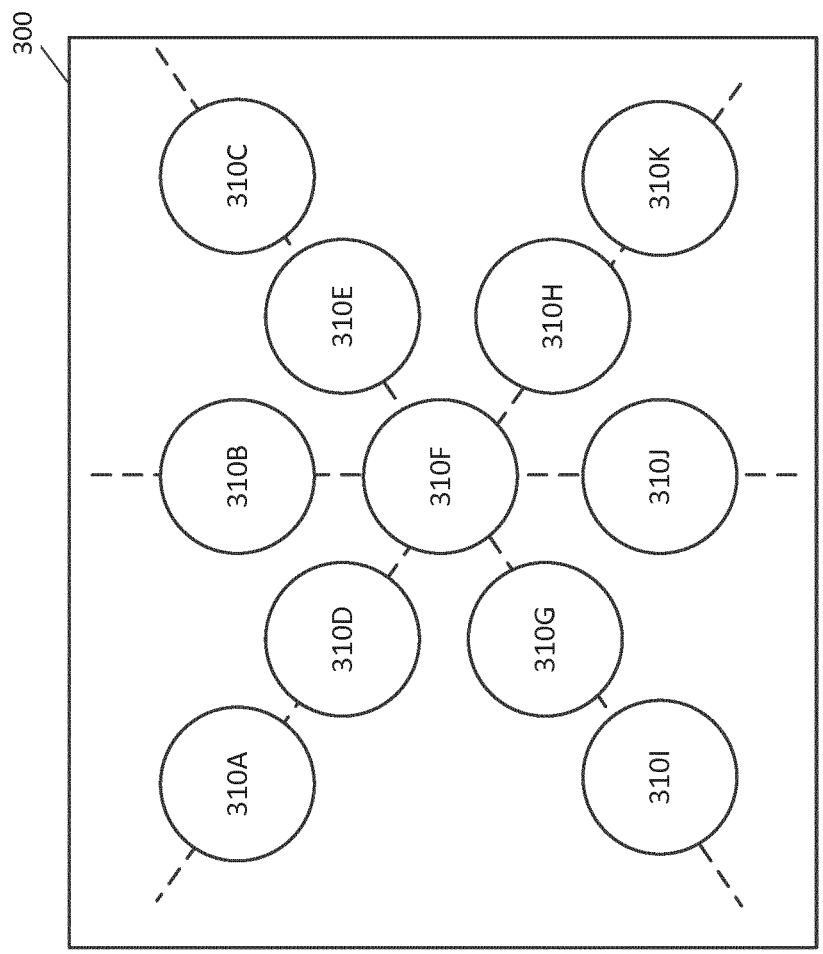
FIGS. 8 and 9 illustrate configurations of the coils arranged in concentric circles with respect to one another or in intersecting rows.

FIG. 8 illustrates a device 300 attachable to a skin of a patient for use in MIT of a tissue of the patient. The device 300 can illustrate one example implementation of the coil(s) and support housing 111 of FIG. 1. The coil(s) and support housing 111 as shown in FIG. 8 includes multiple coils 310A-310K that are part of or contained within a coil housing and arranged in an array. The coil housing can be a material layer that may be flexible and configured to conform to a curvature of the skin. The multiple coils 310A-310K can be arranged in concentric circles with respect to one another or in intersecting rows. In one implementation, the device 300 can be part of a wound dressing or placed underneath a wound dressing used to cover and seal a wound prior to applying negative wound pressure therapy to the wound.

Figure 9:
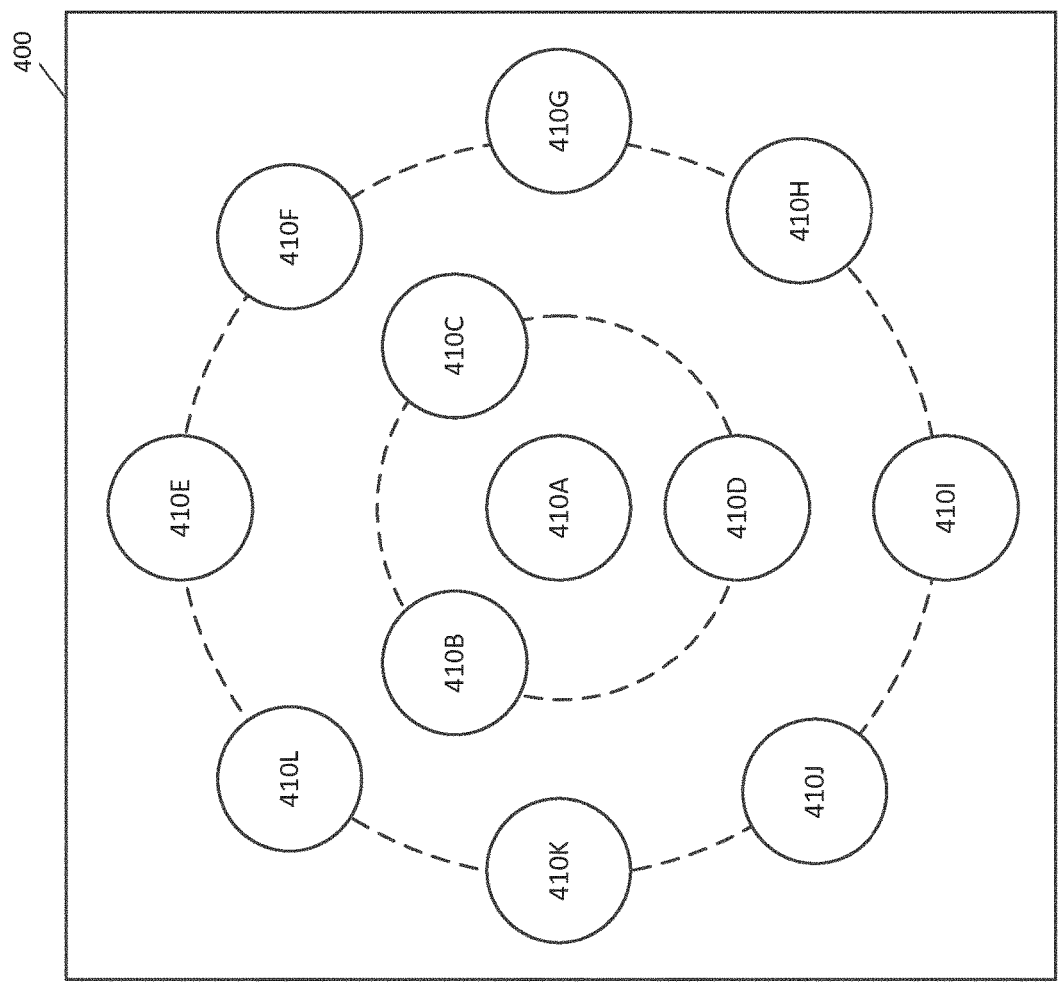

FIG. 9 illustrates a device 400 attachable to a skin of a patient for use in MIT of a tissue of the patient. The device 400 can illustrate one example implementation of the coil(s) and support housing 111 of FIG. 1. The coil(s) and support housing 111 as shown in FIG. 9 includes multiple coils 410A-410L that are part of or contained within a coil housing and arranged in an array. The coil housing can be a material layer that may be flexible and configured to conform to a curvature of the skin. The multiple coils 410A-410L can be arranged in concentric circles with respect to one another or in intersecting rows. In one implementation, the device 400 can be part of a wound dressing or placed underneath a wound dressing used to cover and seal a wound prior to applying negative wound pressure therapy to the wound.

Figure 10:
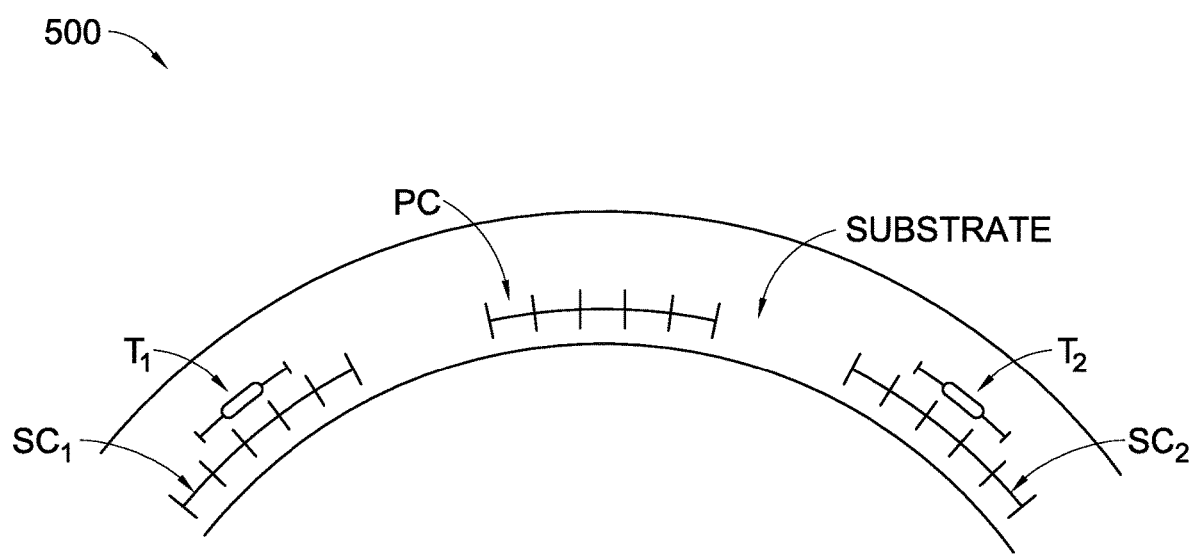
FIG. 10 illustrates a support housing and coils, including a primary coil, secondary coils, and transducers.

FIG. 10 illustrates a device 500 attachable to a skin of a patient for use in MIT of a tissue of the patient. The device 500 can illustrate one example implementation of the coil(s) and support housing 111 and the positioning detector 116 of FIG. 1. The coil(s) and support housing 111 as shown in FIG. 10 includes a primary coil PC and a first secondary coil $SC_1$ and a second secondary coil $SC_2$. The positioning detector 116 includes a first transducer $T_1$ and a second transducer $T_2$. The primary coil PC, the first secondary coil $SC_1$, the second secondary coil $SC_2$, the first transducer $T_1$, and the second transducer $T_2$ can be part of or contained within a substrate. The substrate can be a material layer (for instance, a single or multi-layer) that may be flexible and configured to conform to a curvature of the skin. In one implementation, the device 500 can be part of a wound dressing or placed underneath a wound dressing used to cover and seal a wound prior to applying negative wound pressure therapy to the wound.

The first transducer $T_1$ and second transducer $T_2$ can desirably, in certain embodiments, provide a relatively inexpensive way of performing position detection with the positioning detector 116 (such as in comparison to using a gyroscope). The first transducer $T_1$ and second transducer $T_2$ can be used to detect orientations of one or more of the primary coil PC, the first secondary coil $SC_1$, and the second secondary coil $SC_2$ with respect to one or more of the first transducer $T_1$ and second transducer $T_2$. The first transducer $T_1$ and second transducer $T_2$ can operate at different frequencies with respect to one another in some implementations or at the same frequency but generate different signals with respect to one another in other implementations.

In one example of operating the device 500, the primary coil PC generates a signal at a frequency or frequencies of the first transducer $T_1$. The first transducer $T_1$ response on the primary coil PC and possibly the first secondary coil $SC_1$ and the second secondary coil $SC_2$ can be used, such as by the one or more processors 130, to identify an orientation. Next, the primary coil PC generates a signal at a frequency or frequencies of the second transducer $T_2$, and the second transducer $T_2$ response on the primary coil PC and possibly the first secondary coil $SC_1$ and the second secondary coil $SC_2$ can be used, such as by the one or more processors 130, to identify an orientation. Then, the primary coil PC can perform MIT. Simultaneously or subsequently, the first secondary coil $SC_1$ and the second secondary coil $SC_2$ can perform MIT. Finally, the orientation of the first secondary coil $SC_1$ and the second secondary coil $SC_2$ relative to the primary coil PC can be used to provide a cross-bearing on artifacts when processing the variations to determine electrical properties of the tissue 120.

Figure 11:
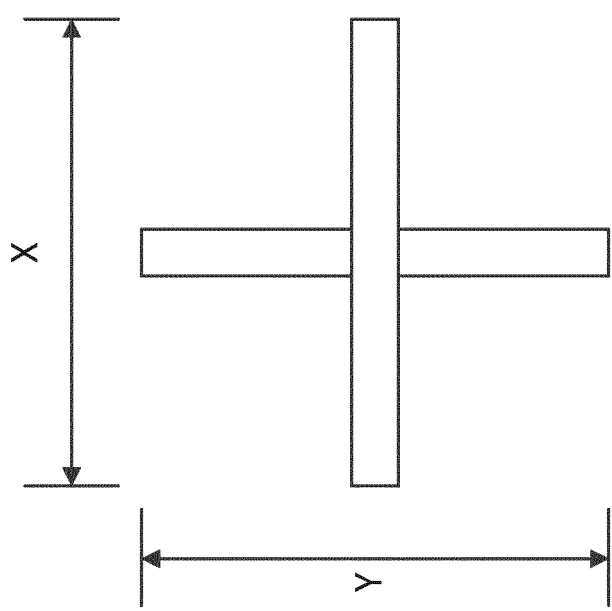
FIG. 11 illustrates a transducer.

FIG. 11 illustrates a transducer 600 that can be used, for example, to perform the function of the first transducer $T_1$ or the second transducer 12. The transducer 600 may resonate at frequencies that are multiples (for instance, 0.5, 1, 1.5, 2, and so on) of the lengths X and Y of the transducer 600. A comparison between the lengths X and Y of the transducer 600 can be used to give an orientation sign.

Additional Embodiments

In some embodiments, a MIT device for imaging a tissue can include a plurality of coils, electronic circuitry configured to separately energize subsets of the plurality of coils to generate a magnetic field perturbed by the tissue, and one or more processors. The one or more processors can be configured to receive MIT signals responsive to the magnetic fields perturbed by the tissue. The one or more processors can also be configured to receive the MIT signals being generated by the plurality of coils, each of at least some of the MIT signals being indicative of a characteristic of the tissue at a different depth in the tissue from a surface of the tissue. The one or more processors can further be configured to process the MIT signals to generate an MIT image. In some embodiments, at least some of the plurality of coils are concentrically arranged with respect to one another.

Some embodiments include the MIT device of any one or more preceding embodiments, wherein the plurality of coils include a stack of coils in which the one or more coils of each level of the stack of coils is vertically spaced from the one or more coils of each other level of the stack of coils, and the electronic circuitry is configured to separately energize each of the plurality of coils by sequentially applying a voltage to the one or more coils of each different level of the stack of coils.

Some embodiments include the MIT device of any one or more preceding embodiments, wherein at least some of the subsets do not include more than one coil.

In some embodiments, a MIT device for imaging a tissue can include: at least one coil; an elongate member coupled to the at least one coil and configured to move in a reciprocating manner to vary a distance of the at least one coil from the tissue; electronic circuitry configured to energize the at least one coil to generate a magnetic field perturbed by the tissue; and one or more processors. The one or more processors can be configured to: receive MIT signals responsive to the magnetic field perturbed by the tissue, the MIT signals being generated by the at least one coil, each of at least some of the MIT signals being indicative of a characteristic of the tissue at a different depth in the tissue from a surface of the tissue, and process the MIT signals to generate an MIT image.

Some embodiments include the MIT device of any one or more preceding embodiments, wherein the elongate member includes a piston.

Some embodiments include the MIT device of any one or more preceding embodiments, wherein the elongate member includes a threaded screw.

In some embodiments, a MIT device for imaging a tissue can include: one or more concentrically arranged coils; a ferromagnetic core extending along an axis of the one or more concentrically arranged coils; an actuator configured to axially move the ferromagnetic core relative to the one or more concentrically arranged coils; electronic circuitry configured to energize the one or more concentrically arranged coils to generate a magnetic field perturbed by the tissue; and one or more processors. The one or more processors can be configured to: receive MIT signals responsive to the magnetic field perturbed by the tissue, the MIT signals generated by the one or more concentrically arranged coils, each of at least some of the MIT signals being indicative of a characteristic of the tissue at a different depth in the tissue from a surface of the tissue, and process the MIT signals to generate an MIT image.

In some embodiments, a MIT device for imaging a tissue can include: one or more coils mounted off-center of an axis of rotation of a rotatable member; an actuator configured to rotate the rotatable member; electronic circuitry configured to energize the one or more coils to generate a magnetic field perturbed by the tissue; and one or more processors. The one or more processors can be configured to: receive MIT signals responsive to the magnetic field perturbed by the tissue, the MIT signals generated by the one or more coils, each of at least some of the MIT signals being indicative of a characteristic of the tissue at a different depth in the tissue from a surface of the tissue, and process the MIT signals to generate an MIT image.

Some embodiments include the MIT device of any one or more preceding embodiments, wherein the one or more coils include at least four coils and are concentrically arranged with respect to one another, and the electronic circuitry is configured to energize each of the one or more coils by sequentially applying a voltage to each different coil of the one or more coils.

Some embodiments include the MIT device of any one or more preceding embodiments, wherein the one or more coils includes a stack of coils in which the one or more coils of each level of the stack of coils is vertically spaced from the one or more coils of each other level of the stack of coils, and the electronic circuitry is configured to separately energize each of the plurality of coils by sequentially applying a voltage to the one or more coils of each different level of the stack of coils.

Some embodiments include the MIT device of any one or more preceding embodiments, wherein the characteristic includes a conductivity of the tissue, a permittivity of the tissue, or a permeability of the tissue.

In some embodiments, a device attachable to a skin of a patient for use in MIT of a tissue of the patient can include: an input port configured to receive a control signal from electronic circuitry; and a material layer including a plurality of coils arranged in an array. The plurality of coils can be configured to: responsive to the control signal, generate a magnetic field perturbed by the tissue, and generate and output an MIT signal responsive to the magnetic field perturbed by the tissue.

Some embodiments include the device of any one or more preceding embodiments, wherein the plurality of coils are arranged in parallel rows.

Some embodiments include the device of any one or more preceding embodiments, wherein the plurality of coils are arranged in concentric circles with respect to one another.

Some embodiments include the device of any one or more preceding embodiments, wherein the plurality of coils are arranged in intersecting rows.

Some embodiments include the device of any one or more preceding embodiments, wherein the material layer is flexible and configured to conform to a curvature of the skin.

Some embodiments include the device of any one or more preceding embodiments, wherein the material layer further includes an orientation detector.

Some embodiments include the device of any one or more preceding embodiments, wherein the orientation detector is configured to detect an orientation of the plurality of coils with respect to the orientation detector.

Some embodiments include the device of any one or more preceding embodiments, wherein the orientation detector includes a plurality of transducers.

Some embodiments include the device of any one or more preceding embodiments, wherein at least some of each of the plurality of transducers are configured to operate at different frequencies with respect to one another, or at least some of each of the plurality of transducers are configured to operate at the same frequency but generate different signals with respect to one another.

Some embodiments include the device of any one or more preceding embodiments, wherein the material layer is configured to be underneath or part of a wound dressing while a source of negative pressure provides negative pressure to the wound dressing.

Some embodiments include the device of any one or more preceding embodiments, further including an output port configured to output the MIT signal to one or more processors.

Some embodiments include the device of any one or more preceding embodiments, wherein the input port and the output port are the same port, or input port and the output port are different ports.

Some embodiments include the device of any one or more preceding embodiments, further including the electrical circuitry and the one or more processors.

Some embodiments include the device of any one or more preceding embodiments, wherein the control signal causes a first subset of the plurality of coils to energize and does not cause a second subset of the plurality of coils to energize.

Some embodiments include the device of any one or more preceding embodiments, wherein for a first duration of time while energizing the plurality of coils, a first subset of the plurality of coils generate and output the MIT signal and a second subset of the plurality of coils do not generate or output the MIT signal.

Some embodiments include the device of any one or more preceding embodiments, wherein the magnetic field is perturbed by a conductivity of the tissue, a permittivity of the tissue, or a permeability of the tissue.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. A magnetic inductance tomography (MIT) device for imaging a tissue of a patient, the MIT device comprising:
   a plurality of coils comprising a first coil and a second coil;
   an electronic circuitry configured to separately energize individual coils of the plurality of coils to generate magnetic fields perturbed by a tissue of a patient;

an elongate member coupled to the plurality of coils and configured to move in a reciprocating manner to vary a distance of the plurality of coils from the tissue; and one or more processors configured to:
receive MIT signals responsive to the magnetic fields perturbed by the tissue, the MIT signals comprising a first MIT signal generated by the first coil and a second MIT signal generated by the second coil, the first MIT signal being indicative of a characteristic of the tissue at a different depth in the tissue from a surface of the tissue than the second MIT signal, and
process the MIT signals to generate an MIT image.

2. The MIT device according to claim 1, wherein the first coil and the second coil are concentrically arranged with respect to one another.

3. The MIT device according to claim 1, wherein the plurality of coils comprise a stack of coils in which one or more coils of each level of the stack of coils is vertically spaced from the one or more coils of each other level of the stack of coils, and the electronic circuitry is configured to separately energize individual coils of the plurality of coils by sequentially applying a voltage to the one or more coils of each different level of the stack of coils.

4. The MIT device according to claim 3, wherein the stack of coils comprise at least three levels of coils.

5. The MIT device according to claim 1, wherein the elongate member comprises a piston.

6. The MIT device according to claim 1, wherein the elongate member comprises a threaded screw.

7. The MIT device according to claim 1, further comprising:
a ferromagnetic core extending along an axis of at least one of the plurality of coils; and
an actuator configured to axially move the ferromagnetic core.

8. The MIT device according to claim 1, further comprising an actuator configured to rotate a rotatable member, the first coil being mounted off-center of an axis of rotation of the rotatable member.

9. The MIT device according to claim 1, wherein the plurality of coils comprise at least four coils that are concentrically arranged with respect to one another, and the electronic circuitry is configured to energize individual coils of the plurality of coils by sequentially applying a voltage to each different coil of the plurality of coils.

10. The MIT device according to claim 1, wherein the characteristic comprises a conductivity of the tissue, a permittivity of the tissue, or a permeability of the tissue.

11. A magnetic inductance tomography (MIT) device for imaging a tissue of a patient, the MIT device comprising:
a plurality of coils comprising a first coil and a second coil, the first coil and the second coil being concentrically arranged with respect to one another;
an electronic circuitry configured to separately energize individual coils of the plurality of coils to generate magnetic fields perturbed by a tissue of a patient; and
one or more processors configured to:
receive MIT signals responsive to the magnetic fields perturbed by the tissue, the MIT signals comprising a first MIT signal generated by the first coil and a second MIT signal generated by the second coil, the first MIT signal being indicative of a characteristic of the tissue at a different depth in the tissue from a surface of the tissue than the second MIT signal, and
process the MIT signals to generate an MIT image.

12. The MIT device according to claim 11, further comprising an elongate member coupled to the plurality of coils and configured to move in a reciprocating manner to vary a distance of the plurality of coils from the tissue, the elongate member comprising a piston or a threaded screw.

13. The MIT device according to claim 11, further comprising:
a ferromagnetic core extending along an axis of at least one of the plurality of coils; and
an actuator configured to axially move the ferromagnetic core.

14. The MIT device according to claim 11, further comprising an actuator configured to rotate a rotatable member, the first coil being mounted off-center of an axis of rotation of the rotatable member.

15. The MIT device according to claim 11, wherein the plurality of coils comprise at least four coils that are concentrically arranged with respect to one another, and the electronic circuitry is configured to energize individual coils of the plurality of coils by sequentially applying a voltage to each different coil of the plurality of coils.

16. A magnetic inductance tomography (MIT) device for imaging a tissue of a patient, the MIT device comprising:
a plurality of coils comprising a stack of coils in which one or more coils of each level of the stack of coils is vertically spaced from the one or more coils of each other level of the stack of coils;
an electronic circuitry configured to separately energize individual coils of the plurality of coils by sequentially applying a voltage to the one or more coils of each different level of the stack of coils to generate magnetic fields perturbed by a tissue of a patient; and
one or more processors configured to:
receive MIT signals responsive to the magnetic fields perturbed by the tissue, the MIT signals comprising a first MIT signal generated by a first coil of the plurality of coils and a second MIT signal generated by a second coil of the plurality of coils, the first MIT signal being indicative of a characteristic of the tissue at a different depth in the tissue from a surface of the tissue than the second MIT signal, and
process the MIT signals to generate an MIT image.

17. The MIT device according to claim 16, wherein the stack of coils comprise at least three levels of coils.

18. The MIT device according to claim 16, further comprising an elongate member coupled to the plurality of coils and configured to move in a reciprocating manner to vary a distance of the plurality of coils from the tissue, the elongate member comprising a piston or a threaded screw.

19. The MIT device according to claim 16, further comprising:
a ferromagnetic core extending along an axis of at least one of the plurality of coils; and
an actuator configured to axially move the ferromagnetic core.

20. The MIT device according to claim 16, further comprising an actuator configured to rotate a rotatable member, the first coil being mounted off-center of an axis of rotation of the rotatable member.

* * * * *